United States Patent [19]
Deans et al.

[11] Patent Number: 5,858,370
[45] Date of Patent: Jan. 12, 1999

[54] BENEFICIAL EFFECTS OF PLANT VOLATILE OILS

[75] Inventors: Stanley Gordon Deans, Ayrshire; Raymond Clifford Noble, Ayr, both of United Kingdom

[73] Assignee: Scottish Agricultural College, Ayr, United Kingdom

[21] Appl. No.: 600,949

[22] PCT Filed: Aug. 22, 1994

[86] PCT No.: PCT/GB94/01833

§ 371 Date: Feb. 20, 1996

§ 102(e) Date: Feb. 20, 1996

[87] PCT Pub. No.: WO95/05838

PCT Pub. Date: Mar. 2, 1995

[30] Foreign Application Priority Data

| Aug. 20, 1993 | [GB] | United Kingdom | 9317347 |
| Feb. 18, 1994 | [GB] | United Kingdom | 9403192 |
| Feb. 18, 1994 | [GB] | United Kingdom | 9403193 |
| Apr. 30, 1994 | [GB] | United Kingdom | 9408693 |

[51] Int. Cl.$^6$ ............................ A61K 35/78
[52] U.S. Cl. ............ 242/195.1; 424/439; 424/464; 424/475
[58] Field of Search ............... 424/195.1, 439, 424/464, 475

[56] References Cited

U.S. PATENT DOCUMENTS 4,980,169 12/1990 Oppenheimer et al. ............... 484/439

FOREIGN PATENT DOCUMENTS

| 0 271 133 | 6/1988 | European Pat. Off. | C09K 15/34 |
| 0 542 398 | 5/1993 | European Pat. Off. | A61K 35/78 |
| 2 570 604 | 9/1984 | France | A61K 9/50 |
| 60-224629 | 11/1985 | Japan | A61K 35/78 |
| 2 195 889 | 4/1988 | United Kingdom | A61K 35/78 |

OTHER PUBLICATIONS

"Promotional Effects of Planet Volatile Oils on the Polyunsaturated Fatty Acid Status during aging", S. G. Deans et al, Age, vol. 16, 1993, pp. 71–74

Natural Antioxidants from Aromatic and Medicinal Plans, S. G. Deans et al., in *Role of Free Radicals in Biological Systems,* 1993, pp. 159–165

International Search Report for PCT/GB94/01833 (priority date: Aug. 20, 1993)

U. K. Search Report for GB2 282 532 (corresponding to the present application) dated 21 Nov. 1994.

*Primary Examiner*—Herbert J. Lilling
*Attorney, Agent, or Firm*—Ratner & Prestia

[57] ABSTRACT

Plant volatile oils have been found to have certain beneficial effects on the body of a human or non-human. The effects described relate to the maintenance of levels of polyunsaturated fatty acids (PUFAs), the prevention or mitigation of deleterious changes in nervous tissue, elevation of protein levels, and the prevention or mitigation of retinal degeneration.

19 Claims, 5 Drawing Sheets

BENEFICIAL EFFECTS OF PLANT VOLATILE OILS

BACKGROUND OF THE INVENTION

This invention relates to the beneficial effects of plant volatile oils in a human or non-human body.

Oils from various sources have been known to have a beneficial effect in humans and animals and can provide vitamins, fats and other life-enhancing chemicals. Examples of such oils are fish oil, such as cod-liver oil.

Plant volatile oils, in particular from *Thymus vulgaris*, have been shown by the inventors to have beneficial effects on various tissues in the body.

From the present data, it appears that at least some of the beneficial effects of plant volatile oils on human or non-human bodies are connected with the levels of polyunsaturated fatty acids (PUFAs) in the bodies.

SUMMARY OF THE INVENTION

According to the present invention there is provided the use of a plant volatile oil or a constituent thereof
  (a) to maintain the levels of PUFAs; and/or
  (b) to combat deleterious changes in nervous tissue; and/or
  (c) to combat changes in the level of a neuropeptide in nervous tissue; and/or
  (d) to produce elevated protein levels; and/or
  (e) to combat the effects of ageing by elevating protein levels; and/or
  (f) to combat protein loss; and/or
  (g) to produce elevated PUFA levels in the retina; and/or
  (h) to combat retinal degeneration
in a human or animal body.

DETAILED DESCRIPTION OF THE INVENTION

The term "plant volatile oil" is used herein to refer to any organic oil or fatty substance derivable from plants by distillation and includes synthetic equivalents of such volatile oils-as well as equivalent oils from other, non-plant, sources. A constituent of a plant volatile oil is any ingredient found in a plant volatile oil which causes or contributes to the effect required in the invention.

The term "combat" as used herein refers to the prevention of a condition (ie prophylactic use) as well as treatment of an existing condition to ameliorate that condition or to delay or prevent its further deterioration.

The "deleterious changes in nervous tissue" mentioned above in part (b) may comprise degeneration of nervous tissue, changes in morphology or structure of nerve cells present in the tissue, reduction in the number of nerve cells present in the tissue, and reduction in nervous tissue function (not necessarily accompanied by morphological changes).

In a preferred aspect the present invention provides the use of a plant volatile oil for the purpose of any of parts (b) to (h) above.

Further according to the invention there is provided the use of a plant volatile oil or a constituent thereof for the manufacture of a medicament for the purpose of any of parts (a) to (h) above.

In another preferred aspect the present invention provides the use of a plant volatile oil for the manufacture of a medicament for the purpose of any of parts (b) to (h) above.

Further according to the invention there is provided a method of
  (a) maintaining the level of PUFAs; and/or
  (b) combatting deleterious changes in nervous tissue; and/or
  (c) combatting changes in the level of a neuropeptide in nervous tissue; and/or
  (d) producing elevated protein levels; and/or
  (e) combatting the effects of ageing by elevating protein levels; and/or
  (f) combatting protein loss; and/or
  (g) producing elevated PUFA levels in the retina; and/or
  (h) combatting retinal degeneration
in a human or animal body, said method comprising administering a plant volatile oil or a constituent thereof to said body.

Preferably, the plant volatile oil is administered in a sufficient concentration to prevent substantial diminution of the level of essential long chain PUFAs of metabolic significance, such as arachidonic acid, eicosapentanoic acid and/or docosohexaenoic acid in the body. The plant volatile oil may be administered in a daily amount of not less than 15 mg per 50 kg of animal body weight, preferably not less than 20 mg per 50 kg and most preferably not less than 25 mg per 50 kg.

Plant volatile oils which have been found to have the beneficial effects stated above are those derivable from clove, nutmeg, pepper, thyme, paprika, oregano, marjoram, basil and French tarragon. Most preferably, the plant volatile oil is derived from thyme or clove. Oils or constituents thereof may be used alone or in combination with other oils or constituents.

The neuropeptide mentioned is generally selected from neuropeptide Y, substance P, somatostatin, vasoactive intestinal polypeptide, serotonin and dopamine B-hydroxylase.

The nervous tissue mentioned may be, but is not limited to, small intestinal neural tissue.

Optionally, the protein levels mentioned in parts (d) and (e) are elevated to the extent that the ratio of creatinine excretion (in mg per 24 hours) to 3-methyl histidine excretion (in $\mu$mol per 24 hours) is reduced by about a factor of 2–3.

The plant volatile oil or constituent thereof may be administered together with a pharmaceutical carrier and may be simply admixed therewith or chemically linked thereto. Alternatively the plant volatile oil or constituent thereof may be administered as an emulsion with an aqueous constituent. If required, the plant volatile oil may be encapsulated.

The plant volatile oil or a constituent thereof may be administered by any suitable route, including enteral, parental or topical administration.

Maintenance of PUFA levels in the retina has a beneficial effect on the retina, reducing the rate of retinal degeneration (due to age or other conditions).

"Retinal degeneration" refers to any condition which affects the retinal structure and/or causes an effect on vision. Mention may be made of age-related macular degeneration (AMD) as being an important example of visual impairment.

Hepatic damage due to intake of free-radical inducing compounds such as solvents and alcohol may be minimised by the administration of plant volatile oils.

The PUFA status in the foetus/neonate is as important as that in the elderly. Due to the small molecular weight of the oil constituents, it appears likely that they will cross the placenta from mother to foetus, enabling protection from a very early stage of development.

EXAMPLE 1

Figure 1:
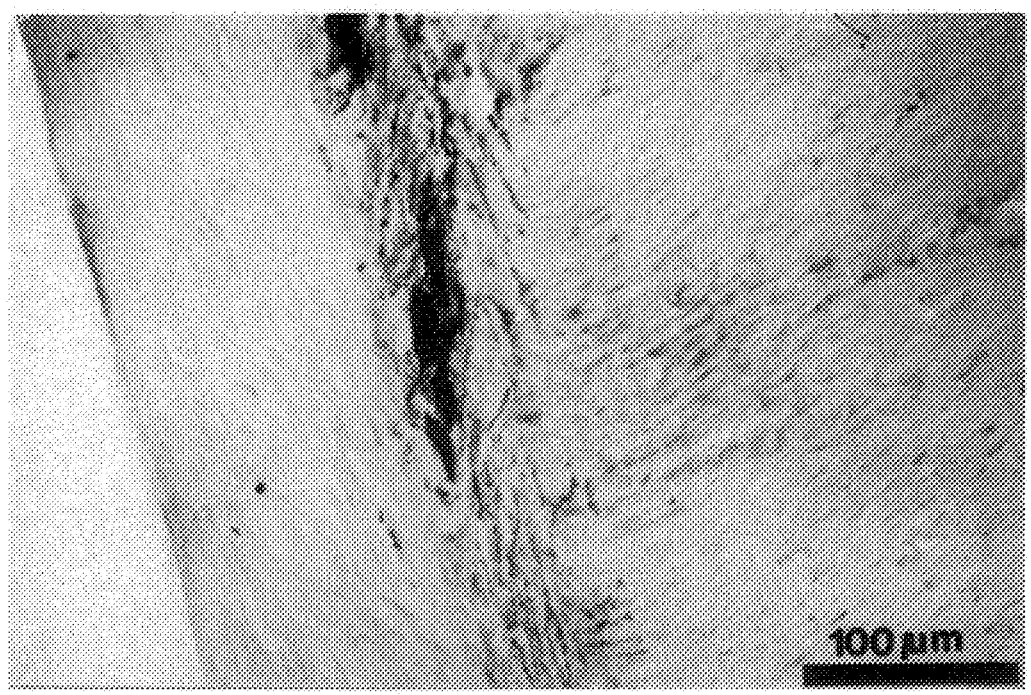
FIG. 1 is a light microscopic picture of the neuropeptide Y immunoreactive nerve cell bodies and fibres in the myenteric plexus of a control animal (bar scale=100 μm)

The use of plant volatile oils to maintain levels of PUFAs.

Preliminary screening of plant volatile oils showed thyme oil and a number of its constituent compounds to possess strong antioxidative properties and thereby to increase levels of PUFAs. The five most active constituents were linalool, thujone, camphene, carvacrol and thymol.

Materials and Methods

Test Animals

The studies were performed on groups, 10 in each group, of young (6 month) and ageing (22 month) in-bred male CBA/Ca mice (LATI, Gödöllö, Hungary). The mice were housed in standard plastic cages. The mice were fed a standard laboratory pelleted diet of uniform lipid quantity and quality (LATI, Gödöllö, Hungary) which, with tap water, was available ad libitum. The treated mice each received for a duration of five weeks (young mice) and 21 weeks (ageing mice) 720 μg of the plant volatile oils administered orally every second day, via a dropper. The dose, following appropriate dilution with drinking water, was emulsified using a vortex mixer. The doses of volatile oils received by the treated mice were based on formulae worked out from the relative proportions of intensive growth and the plateau of relatively constant body weight experienced by the CBA/Ca mice exhibiting a median survival of <24 months. The untreated groups of mice received only water. Death was by decapitation and the livers were immediately removed for analysis.

Volatile Oils

Plant volatile oils were obtained from Serva, Heidelberg, Germany. Volatile oils of almond, clove, nutmeg, pepper and thyme were stored in the dark at 4° C. until used. The antioxidative capacity was determined qualitatively by a simple agar diffusion technique of Arujo and Pratt using β-carotene and linoleic acid. Test substances were placed in wells (4 mm in diameter) punched in the agar (Oxoid, Basingstoke, England) followed by, incubation, in the dark, at 45° C. for 4 hours. Subsequent inspection of the plates revealed the extent to which the volatile oils were antioxidative as measured by the zone of colour retention around the well. Corroborative evidence of the antioxidant capacity was achieved by using the thiobarbituric acid technique and comparing with butylate hydroxyanisole (BHA) at the same concentration.

Lipid Analysis

Total lipid was extracted from homogenates of the livers by chloroform:methanol (2:11, v/v) and subsequent aqueous washing according to standard procedures. Total phospholipid was separated by thin layer chromatography on silica gel by using a solvent system of hexane:dimethyl ether:formic acid (80:20:1, v/v/v). Following visualisation under UV light, the phospholipid was quantitatively eluted from the silica gel with 3×10 ml of chloroform:methanol:water (5:5:1, v/v/v/). Following transesterification by refluxing with methanol:toluene:sulphuric acid (20:10:1, v/vv/v), the fatty acids were determined as their methyl ester derivatives by gas liquid chromatography on a packed column of 15% CP Sil 84 on Chromosorb W (Chrompak, Middleburg, The Netherlands) at 190° C. Quantification of the fatty acid peaks was by electronic integration.

Results

The relative concentrations of the major individual fatty acids within the phospholipid fractions of the livers from the young and ageing mice are given in Table 1.1. Treatment with volatile oils had no effect on the fatty acid composition of the liver phospholipids from the young mice. Comparison of the fatty acid composition of the phospholipids from the young untreated mice with those from the 22 month-old untreated mice show clearly a large effect of ageing on the relative level of saturation/unsaturation within the fatty acids. Total levels of the major C20 (arachidonic) and C22 (docosohexaenoic) polyunsaturated fatty acids were more than halved being reduced from 22% to only 9% of total fatty acids. A smaller reduction occurred in the level of linoleic acid while there was a compensatory increase in the level of palmitic acid. Dietary administration of the volatile oils to the ageing mice clearly had a marked effect on fatty acid distribution by virtually restoring the proportions of the polyunsaturated fatty acids within the phospholipids to their levels observed in the young mice. With phospholipids being a predominant component of the total liver lipid, and by far the major carrier of polyunsaturated fatty acids, in particular the C20 and C22 polyunsaturated fatty acids, the observations therefore reflected polyunsaturated fatty acid compositional changes in the liver as a whole.

By using the simple diffusion test for antioxidative properties, a number of thyme oil constituents have been studied (Table 1.2). Thujone, linalool, camphene, δ-terpinene, β Caryophylene, borneo, myrcene, thymol and carvacrol all had zones of colour retention in excess of 10 mm.

As part of the balance between pro- and antioxidant factors in tissue metabolism, the levels of polyunsaturated fatty acids play a vital role in determining their own destiny. From the present observations, it appears that factors present within specific plant volatile oils, notably thyme, can alter significantly this balance in favour of tissue retention of polyunsaturated fatty acids.

Furthermore, in animals fed with plant volatile oils, elevated levels of the enzyme glutathione peroxidase (GP) and superoxide dismutase (SOD), key enzymes in the protection against oxidation of lipids, were found.

The antioxidative compounds do not necessarily reside in the volatile oil fraction; for example, the oils from *Rosmari-*

*nus officinalis* and *Salvia officinalis* do not demonstrate any strong antioxidative properties, yet these two plants are among the most-quoted species in terms of possessing antioxidants (Table 1.3). A number of solvent extractions (hexane, dichloromethane, ethanol and chloroform) were made on dried plant material and evaluated by the screen described earlier. This revealed a wider range of antioxidant-containing species.

EXAMPLE 2

Effects of plant volatile oils on nervous tissue.

Changes in the number and the distribution of the different nerve elements in old rats were studied after a four month treatment of thyme essential oil using various antisera with the aid of light and electron microscopy. In the control (untreated) animals a number of the different neuropeptide-containing nerve fibres were found in all layers of the small intestine. They were frequently observed around the blood vessels, in the inner circular layer and beneath the epithelial lining. After thyme oil treatment, the quantity of the immunoreactive nerve fibres was more apparent than that of the old controls. The number of the neuropeptide Y and dopamine β-hydroxylase neurolal processes were increased in comparison to the untreated old rats.

Materials and Methods

RLEF1/LATI female rats of 26 months of age, weighing 380 g were used. One group of animals was given via dropper orally every second day 2.4 mg/100 g bw of volatile oil from *Thymus vulgaris* L. (Serva, Heidelberg, Germany). For application, the oil was emulsified to an appropriate dilution with drinking water using a vortex mixer before use. The rats received this volatile oil for a period of four months.

The second group of animals, controls, received tap water only. The rats were fed ad libitum a standard laboratory diet (LATI, GOdöllö, Hungary) throughout the experiment and tap water was freely accessible.

At the end of the experimental period, the animals were sacrificed by decapitation and the tissues immediately isolated and perfused with fixative containing 2% paraformaldehyde, 0.1% glutaraldehyde and 150 ml saturated picric acid in 0.1M phosphate buffer (pH 7.3). Pieces of the small intestine were removed and placed overnight in glutaraldehyde-free fixative at 4° C. Sections, 40 μm thick, were cut with a Vibratome and the sections rinsed over a period of 24 h in several changes of phosphate-buffered saline.

Immunostaining was performed according to the peroxidase-antiperoxidase (PAP) technique of Sternberger et al (1970). After peroxidase reaction, the sections were post fixed in osmium tetroxide and embedded in Durkupan ACM (Fluka, Switzerland). The primary antisera were diluted 1:500 or 1:5000. Incubation was performed at 4° C. for 48 h. Normal serum and PAP were used in dilutions 1:50. The following antisera were used: neuropeptide Y (NPY), substance P (SP), somatostatin, vosoactive intestinal polypeptide (VIP), serotonin and dopamine β-hydroxylase. All antisera were raised in rabbits. Tissue-bound peroxidase was visualised with the diaminobenzidine (DAB) chromogen reaction.

In the controls, complete lack of staining was found following assessment under conditions of: (1) Omission of the primary antibody; (2) Incubation with primary antibody preabsorbed (12–24 h at 4° C.) with appropriate peptide or other peptides, at a concentration of 10 μM.

Results

Figure 2:
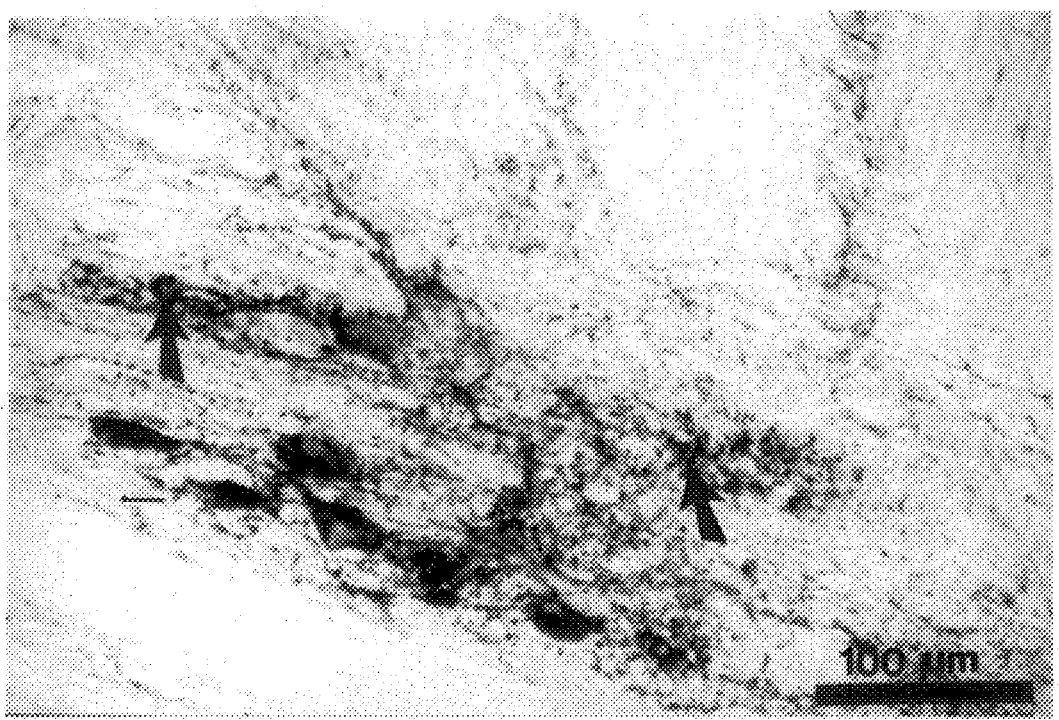
FIG. 2 shows a part of a myenteric plexus after treatment with thyme oil, arrows show the large number of neuropeptide Y immunoreactive nerve fibres (bar scale=100 μm)
Figure 3:
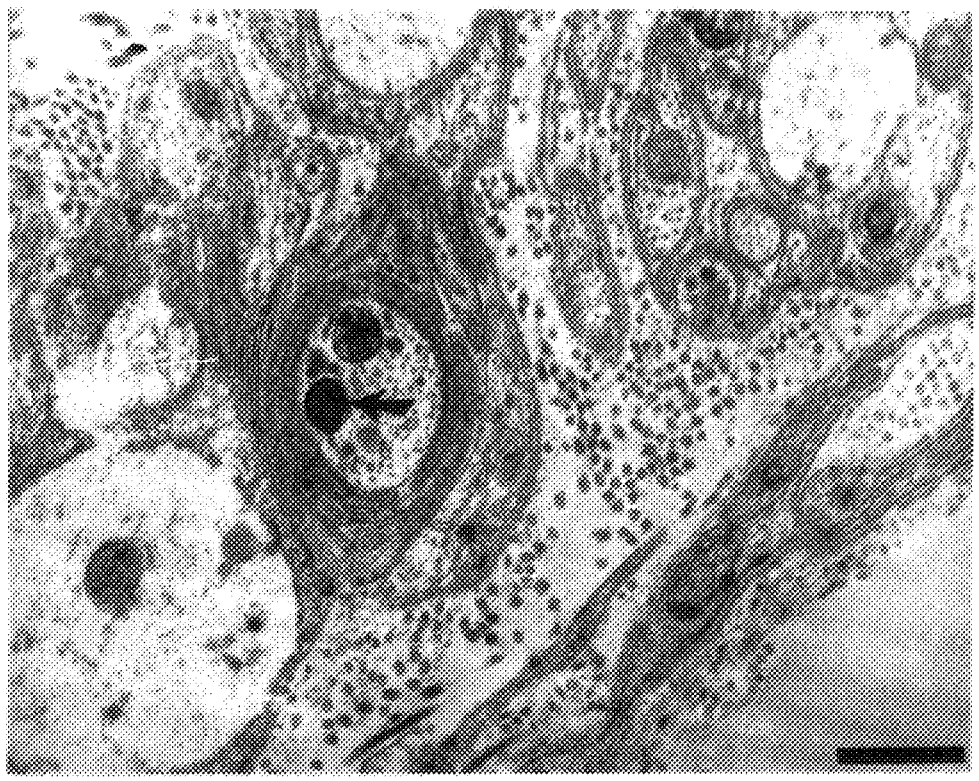
FIG. 3 shows a part of the nerve bundle from aged controls, the arrow points to the degenerated nerve fibre among the unstained ones (bar scale=1 μm)

In the control (untreated) rat, the NPY immunoreactive nerve elements were most numerous in all layers, but especially around the blood vessels (FIG. 1). Thyme oil treatment resulted in an increased quantity of immunoreactive nerve processes compared to the untreated controls (FIG. 2). Under electron microscopic investigation, in the control animals the majority of the nerve fibres displayed a general lack of staining and in many instances there was an apparent degenerative condition (FIG. 3). Innervation by SP was associated with a homogeneous distribution of somatostatin, but the somatostatin immunoreactive nerve fibres were more numerous compared to those of SP immunoreactive ones. SP-containing nerve fibres were found in all layers of the small intestine except the outer longitudinal muscle layer. Small bundles of SP-containing nerve fibres were visualised running along the submucosal blood vessels. Numerous immunreactive nerve cell bodies were observed in the myenteric plexus but only a few were found in the submucous plexus.

Figure 4:
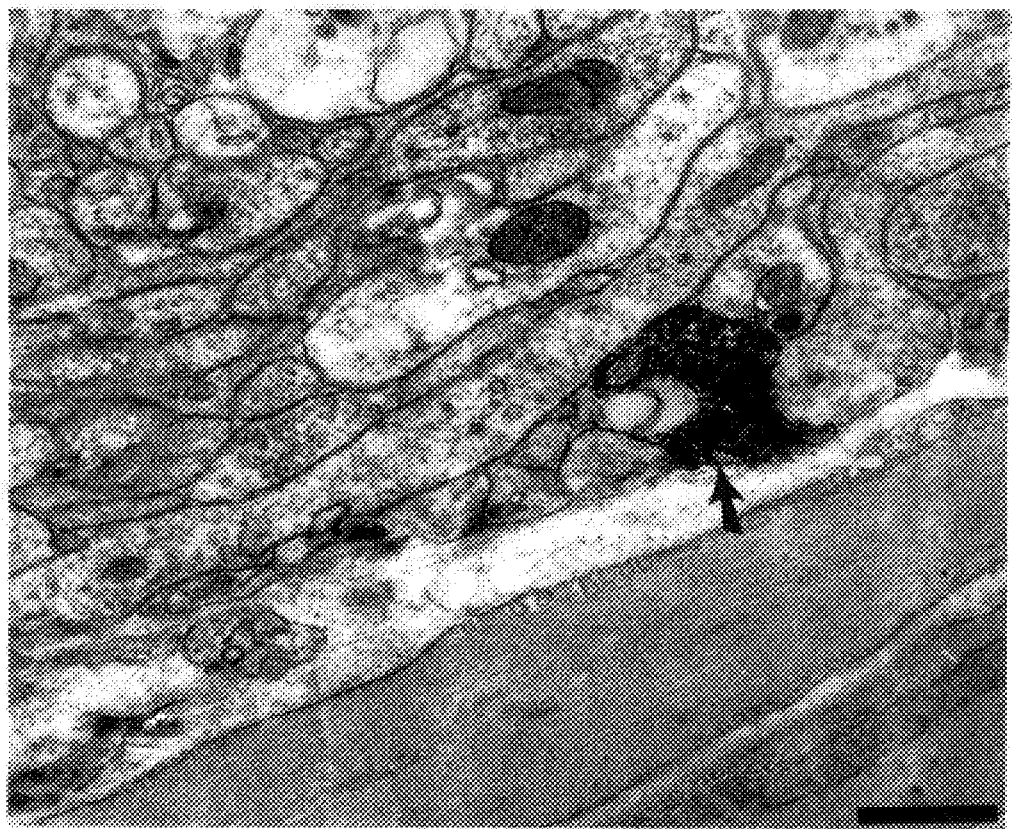
FIG. 4 shows part of the inner circular layer after treatment of *Thymus vulgaris* volatile oil, the arrow shows the somatostatin immunoreactive nerve fibre close to the smooth muscle cell (bar scale=1 μm)
Figure 5:
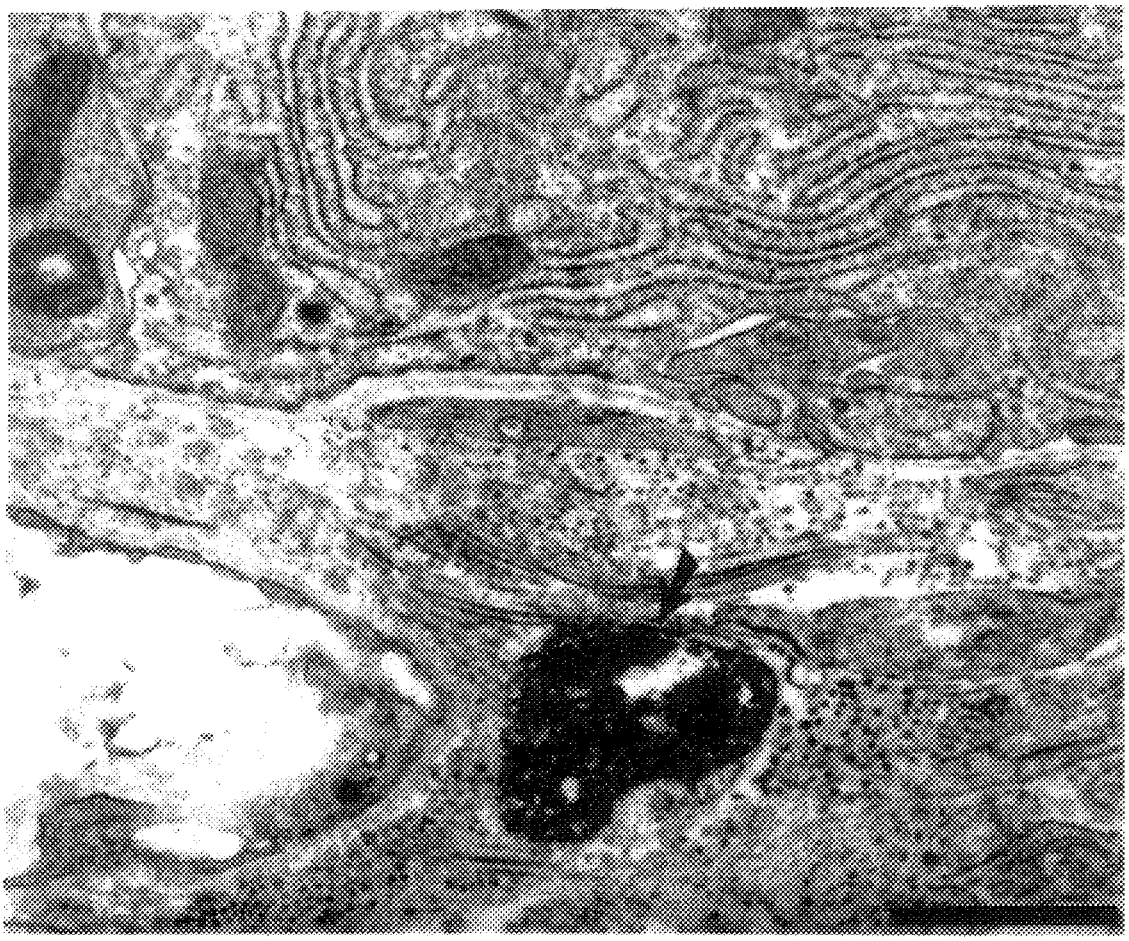
FIG. 5 shows a part of the tunica mucosa of the small intestine after thyme oil treatment, the arrow points to the vasoactive intestinal polypeptide (VIP) immunoreactive nerve fibre in a very close situation to a capillary (bar scale=1 μm)

After thyme oil treatment, nerve fibres either singly, a few together or in small bundles, were observed running along the smooth muscle cells in the circular muscle layer (FIG. 4). Somatostatin nerve cell bodies were found to predominate in the submucous plexus. Stained profiles were found to be located in the core of the villi and in the connective tissue distributed among the crypts, opposed to epithelial cells, the endothelial cells of blood vessels or smooth muscle cells. VIP immunoreactive nerve cell bodies were found mainly in the myenteric plexus. A large number of VIP immunoreactive nerve fibres were observed around the blood vessels in the thyme oil treated animals (FIG. 5). Conventional synaptic junctions between the labelled and unlabelled nerve cell somata were rarely seen in both plexa. Serotonin immunoreactive nerve profiles were seldom observed. Dopamine β-hydroxylase immunoreactive nerve fibres were routinely seen around the blood vessels in all layers of the small intestine.

For all animals, areas of 5000–6500 μm$^2$ of intestinal tissue were examined and the number of immunoreactive nerve terminals was calculated for 1000 4 μm$^2$ tissue area. In the thyme oil treated rats, the number of NPY and dopamine β-hydroxylase immunoreactive neuronal processes was apparently increased in the experimental animals in comparison with the untreated rats (Table 2.1).

TABLE 2.1

Influence of a plant essential oil (*Thymus vulgaris* L) on the immunoreactive nerve fibres in the small intestine (number/1000 μm$^2$ tissue area).

| Animal | VIP | NPY | SP | Serotonin | DBH |
| --- | --- | --- | --- | --- | --- |
| Control | ++++ | +++ | ++++ | + | + |
| Treated | +++ | ++++ | ++++ | + | ++ |

The number of fibres identified with the antibodies has been expressed semi-quantitatively from single (+ = 1–5), moderate (++ = 6–10), numerous (+++ = 11–15) to very dense (++++ = >16 fibres/1000 μm$^2$ tissue area).

Discussion

The present data shown that following long term dietary treatment with thyme oil there was an increase in the number of immunoreactive nerve fibres within the submucous plexus. As a result, it can be proposed that dietary intake of thyme oil exerts a beneficial effect on the quantity of the different neuronal elements of the small intestine during ageing. Marked decreases were noted in the activity and amounts of the immunoreactive nerve elements in all layers of the intestinal walls of senile rats.

It has already been shown that free radicals damage the cells mainly by initiating peroxidation of membrane lipids (Halliwell, 1981). The immunoreactive nerve terminals seem to be a target of this process. Indeed, it has been suggested that one of the consequences of free radical attacks could be the marked change in molecular composition of the myelin with ageing (Malone and Szoke, 1992). Most notably this has been observed to include a modified ratio between the unsaturated and saturated long-chain fatty acids.

The present results show that plant essential oils may be capable of mitigating these damaging effects.

EXAMPLE 3

The beneficial effect of plant volatile oils on the retina.

Age-related macular degeneration (AMD) is one of the leading causes of severe visual impairment in European counties and the United States of America (Vinding et al, 1992). The primary lesion appears to be in the retinal pigment epithelium (RPE) as the result of a continuous accumulation of lipofucsin granules during ageing. One possible explanation for a predilection to AMD is an increased phagocytotic and metabolic load on the RPE within the macula giving rise to a preferential accumulation of lipofucsin in these cells and ultimately to photoreceptor death (Dorey et al, 1989).

The etiology of AMD is at present unknown. Numerous risk factors are known to be involved that include family history, ocular pigmentation, elastic degeneration of the skin, hyperopia, cardiovascular disease and cigarette smoking (Vinding et al 1992: Blumenkranz, Russell and Robey 1985). Nutritional factors may also contribute to AMD. Thus whereas zinc is an essential element for normal metabolism its toxic side effects have been implicated in AMD (Tsao, 1985: Newsome et al 1988).

Materials and Methods
Animals

Eleven month old female LATI rats (Gödöllö, Hungary) were randomly assigned into control and 5 treatment groups each of 6 animals. The rats received a standard pelleted diet which with water was available ad libitum. The treated animals each receive via a dropper for a period of 17 months an appropriate volume of a water emulsion containing 7.7 mg of plant volatile oil, administered orally every second day; the control group received water only. The plant oils—almond clove, nutmeg, pepper and thyme (Serva, Heidelberg, Germany)—were stored in the dark at 4° C. until used. Maintenance of their antioxidative capacities was monitored by the agar diffusion technique described previously. The rats were killed at 28 months of age and following rapid enucleation, the retinas were excised and immediately stored in liquid nitrogen to await analysis. To enable sufficient lipid material to be obtained; all the retinas from each treatment group were pooled for analysis.

Lipid analysis

All chemicals used were of the highest specification. Total lipid from the retinas was extracted by established procedures involving chloroform-methanol (Folch, Lees and Stanley, 1957), the lipid ultimately being taken up in benzene containing 0.25 percent (W/v) α-tocopherol as an antioxidant. The liquid was then fractionated by stepwise mini-column silicic acid/celite chromatography into 3 discrete fractions, total neutral lipid, glycolipid and total phospholipid, by elution with suitable aliquots of chloroform, chloroform:methanol (9:1 v/v) and pure methanol respectively. Total phospholipid was transmethylated by alkaline reduction (Piretti et al 1988) and following purification by thin layer chromatography, the fatty acid methyl esters were quantified by gas chromatography on a fused silica polar capillary column using an appropriate temperature programming and electronic integration. Confirmation of the identification of the fatty acid methyl ester was performed by separation as above but in conjunction with mass spectrometry.

Results

There was no significant difference in the percentage distribution of the eluted retinal lipid fractions between the groups of rats with phospholipid accounting for 24.2±4.1 (S.E) percent of total lipid separated. Table 3.1 shows the distribution of the unsaturated fatty acids (major acids, percent of total present) associated with the phospholipid fraction of the retinas from the rats following treatment. As can be seen the 3 major unsaturated fatty acids by far in all treatment groups were oleic, arachidonic and docosahexaenoic acids accounting for in excess of 80 percent of the total with docosahexaenoic acid predominating in each case. Treatment with the volatile oils from clove, nutmeg, pepper and thyme all increase markedly the proportion of total polyunsaturated fatty acid, accounted for in each case by very substantial increases in the levels of both arachidonic and docosahexaenoic acids with concomitant large decreases in the levels of palmitoleic and oleic acids. There was also a decrease in the level of linoleic acid.

Polyunsaturated fatty acids comprised by far the major proportion of the total unsaturated content within the retinal phospholipids or the 28 month rats with docosahexaenoic acid predominating. The administration daily of 3.4 mg of the volatile oils from clove, nutmeg, pepper and thyme over a period of 17 months resulted in the maintenance of very much higher levels of polyunsaturated fatty acids, in particular docosahexaenoic acid, within the retinal phospholipids. This increase occurred mainly at the expense of a reduction in the level of oleic acid.

The present observations sustain the suggestion of the involvement of an antioxidant role in retinal function during ageing. The essential oils of clove, nutmeg, pepper and thyme all afforded considerable protection in the maintenance of polyunsaturated fatty acid levels, in particular the highly labile docosahexaenoic acid.

As the n-3 polyunsaturated fatty acids, in particular docosahexaenoic acid, are essential for the normal electrical response in visual excitation (Neuringer, Anderson and Connor, 1988) a decrease in their concentrations must play an important role amongst the causes of visual impairment which accompany senescence. There is no proven treatment for AMD except laser photocoagulation in choroidal neovascularisation. The present invention is therefore of significance from both clinical and therapeutic points of view.

EXAMPLE 4

The beneficial effects of plant volatile oils on protein levels.

Groups of rats were dietarily administered regular small doses of a selection of plant volatile oils between 28 and 45 months of age. Treatment with the oils resulted in an enhancement of whole body weight and overall reductions in specific organ to whole body weight. Urinary excretion of 3-methyl-histidine was reduced in all cases but particularly in those rats that received the volatile oils from clove and thyme. Myofibrillar protein breakdown was also most reduced by the oils from clove and thyme.

Measurements of the overall rates of protein synthesis and degradation in muscle are able to establish existing states of protein metabolism. A wide variety of physiological and pathological conditions have been identified under which muscle becomes a subject of net protein breakdown due to the rate or protein degradation exceeding thank of synthesis (Tischler, 1981).

Materials and Methods
Animals

Female RLEF1/LATI rats (Gödöllö, Hungary), 28 months of age, were the subject of the experiments. The rats were matched for weight and each received ad libitum a standard laboratory compounded diet with a protein content of 20.2 percent; tap water was freely available. The rats were randomised into control and experimental groups, the latter to receive long term dietary treatment with a single plant volatile oil. The oils were bitter almond, clove, nutmeg, pepper and thyme (Serva, Heidelberg, Germany). In each case the oil was emulsified with water and given 3 times per week via a dropper at a rate of 7.7 mg for a period of 17 months. At the completion of the dietary period the rats were killed by decapitation and the major organs excised for analysis.

Analysis

Protein metabolism was monitored through comparative outputs of 3-methyl-histidine and creatinine as detailed previously (Albrecht et al, 1992). Urine samples were prepared for the quantification of 3-methyl-histidine by precipitation of the protein with perchloric acid and following washing, neutralisation with potassium hydroxide, lyophilisation; hydrolysis with 6N hydrochloric acid and finally evaporation to dryness. Samples were stored frozen in sodium citrate buffer, pH 2.2 prior to analysis. Norleucine was used as an internal standard, 3-methyl-histidine was separated by means of ion exchange (Aminex A5, Bio-Rad, Germany) high performance liquid chromatography (Waters millipore, Germany) with post column ninhydrin derivatisation (Spackman et al, 1958). The eluate was channelled into an automatic analyser (ADM 300, Medingen, Germany) for the detection of ninhydrin positive compounds. Creatinine was quantified by a modified Jaffe procedure.

Statistical differences between means were investigated by the Students' t-test and those among more than 2 means by applying the Newman-Keuls multiple range test when the analysis of variance gave a significant ($P<0.05$)F-value.

Results

Table 4.1 shows the whole body and individual organ weights of the rats following treatment for the period of 17 months. As can be seen, the administration of the various plant oils considerably enhanced whole body weight compared to untreated controls; the increases ranged from 22 percent in the case of the rats that received treatment with the volatile oil extract from pepper to 43 percent in the rats that received the volatile oil from nutmeg.

Figure 6:
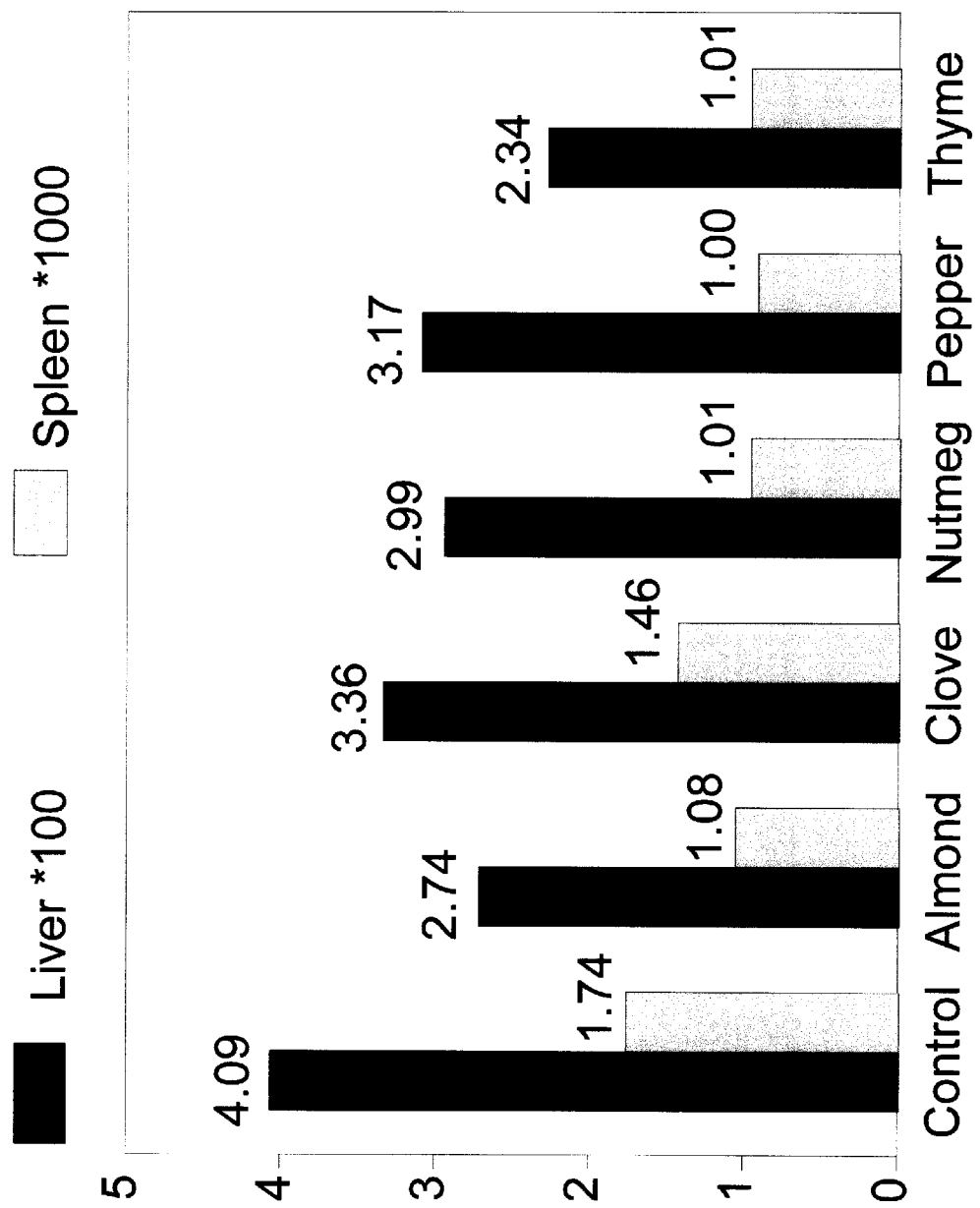
FIG. 6 shows a graph of the ratio of organ weight to whole body weight in rats following treatment with plant volatile oils (mean±standard deviation)

As exemplified by the liver and spleen (FIG. 6), treatment with the volatile oils reduced overall the ratio of specific organ weight to whole body weight.

Table 4.2 shows the measurements for the rates of excretion of 3-methyl-histidine both in absolute amounts per unit period of time and per unit of body weight and standardised relative to the excretion rate of creatinine. It is clear that in terms of body mass, treatment with the volatile oils other than that of nutmeg caused a reduction in the excretion of 3-methyl-histidine. When related to that of creatinine, the excretion of 3-methyl-histidine was reduced in all cases of oil administration but in particular as a result of treatment with that from clove and thyme for which the reductions in excretion were significant, $P<0.05$ and $P<0.01$ respectively.

Figure 7:
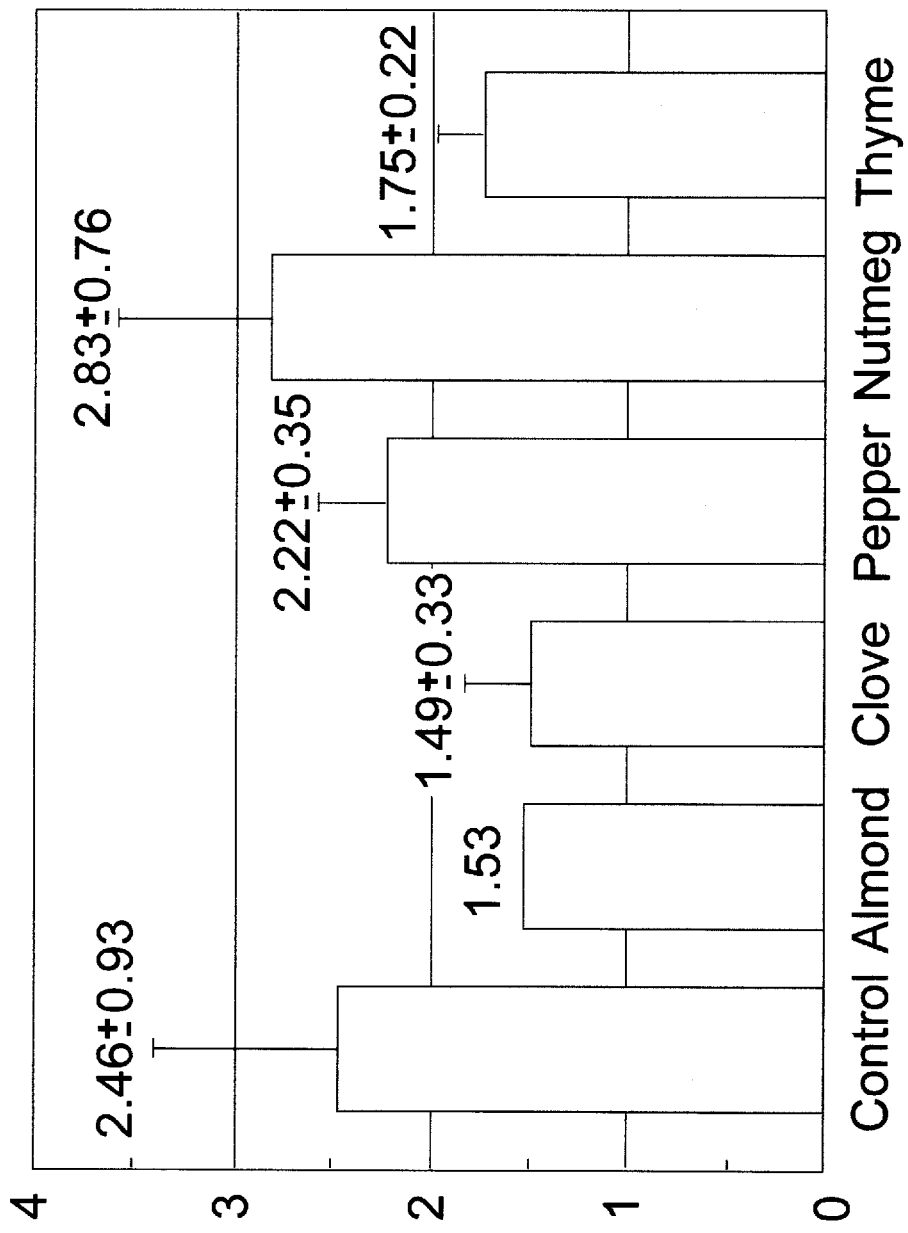
FIG. 7 shows a graph of the ratio of degradation percent per day of myofibrillar protein in rats following treatment with plant volatile oil (mean ±standard deviation).

FIG. 7 shows the values obtained for the fractional rates of degradation of myofibrillar protein as a result of the treatment with the volatile oils. As in the case of overall excretion, treatment with the volatile oils other than that of nutmeg reduced myofibrillar protein breakdown with the largest effect occurring as a result of treatment with oils from clove and thyme.

The present results clearly indicate that the dietary administration of plant volatile oils, in particular those from clove and thyme, display a sparing effect on the metabolism of senile rats in favour of body mass retention.

A combination of urinary creatinine and 3-methyl-histidine quantifications is able to provide an accurate index of muscle protein turnover, the creatinine measurements providing a reliable indicator of the quantity of muscle protein mass (Forbes and Bruining, 1976) and 3-methyl-histidine, because of its specific association with the muscle, an indicator of protein breakdown (Yong and Munro, 1978). Indeed the decline in muscle mass based on creatinine output with age has been shown to be similar to the decrease in the rate of muscle protein turnover based on urinal 3methyl-histidine excretion (Prothro, 1989).

In quantitative terms the level of 3-methyl-histidine excretion is dependent upon the combination of the rate of muscle catabolism and muscle pool size, although circumstances have been demonstrated under which increased protein turnover occurred but which was not associated with increased nitrogen loss (Wilson et al, 1981). In rats, as in a range of other animal species, it has been established that increasing age in accompanied by an overall decrease in the rate of myofibrillar protein degradation (Santidrian et al, 1981). It is clear from the present measurements of 3methyl-histidine outputs that administration of plant volatile oils reduced significantly muscle protein breakdown.

Modifications and improvements may be incorporated without departing from the scope of the invention.

REFERENCES

The following documents are incorporated herein by reference:

Al Jalay, B., Blank, G., McConnell, B., and Al Khayat, M. Antioxidant activity of selected spices used in fermented meat sausage. *J. Food Protect.,* 50:25.

Araujo, J. M. A, and Pratt, D. E. A simplified plate diffusion technique for the determination of lipid antioxidant activity. *Cientia Tecnol Ailment:* 5: 57–60, 1985.

Ballard, F. J. and Tomas, F. M. (1983). 3-methylhistidine as a measure of skeletal muscle protein breakdown in human subjects: The case for its continued use. *Clin. Sci.,* 65, 209–215.

Blumenkranz, M. S. Russel, S. R. and Robey, M. G. (1985). Risk factors in age-related maculopathyy. complicated by choroidal neovasularization. *Ophthalmology* 93, 552–557.

Bourre, J. M., Piciotti, M. and Dumont, O. (1990) Δ-6 desaturase in brain and liver during development and ageing. *Lipids* 25, 354–356.

Chen Y., Zheng R., Jia Zh and Ju Y (1990). Flavonoids as superoxide scavengers and antioxidants. *Free Rad Biol Med* 9, 19–21.

Christie, W. W., Lipid Analysis, Pergamon Press, Oxford, 1982.

Dorey, C. K., Wu G. Ebenstein, D. Garsd A. and Weiter, J. J. (1989). Cell loss in the ageing retina. *Invest. Opthalmol Vis. Sci,* 30, 1691–1699.

Fehér E., Pénzes L. (1987). Density of substance P, vasoactive intestinal polypeptide and somatastatin-containing nerve fibres in the ageing small intestine of the rats. *Gerontology,* 33, 341– 348.

Folch, J., Lees, M. and Stanley, G. M. S. (1957). A simple method for the isolation and purification of total lipids from animal tissues. *J Biol. Chem* 226, 497–509.

Forbes, G. B. and Bruining, G. J. (1976). Urinary creatinine excretion and lean body mass. *Am. J. Clin. Nutr.,* 29, 1359–1366.

Galli. C. and Simopoulas. A. P. Dietary W3 and W6 Fatty Acids: Biological Effects and Nutritional Essentially: *Plennum Press, New York* 1989.

Gecha, O. M. and Fagan, J. M. (1992). Protective effect of ascorbic acid on the breakdown of proteins exposed to hydrogen peroxide in chicken skeletal muscle. *J.Nutr.* 122, 2097–2093.

Gersowitz, M., Munro, H. N., Updall, J. and Young V. R. (1980). Albumin synthesis in young and elderly subjects using a new stable isotope methodology: response to level of protein intake. *Metabolism,* 29,1075–1086.

Goldberg, A. L., Tischler, M., DeMartino, G. and Griffin, G. (1980). Hormonal regulation of protein degradation and synthesis in skeletal muscle. *Fed. Proc.,* 39,31–36.

Goldspink, D. F., Lewis, S. E. M. and Kelly, F. J. (1985). Protein turnover and cathepsin B activity in several individual tissues of foetal and senescent rats. *Comp. Biochem. Physiol.,* 82B, 849–853.

Gurr, M. I., Robinson, M. P., and James, A. T. The mechanism for formation of polyunsaturated fatty acids by photosynthetic tissue. *Eur. J. Biochem.,* 9:70–78,1969.

Hall, D. A., and Burdett, P. E. Age changes in the metabolism of essential fatty acids. *Biochem. Soc. Trans.,* 3:42–46, 1975.

Halliwell B (1981). The biological effects of the superoxide radical and its products. *Bul Eur Physiopath Resp* 17 (Suppl) 21–28.

Harman D. (1968). Free radical theory of ageing. Effect of free radical reaction inhibitors on the mortality rate of male LAF1 mince. *J Gerontol* 23,476–482.

Hayes, K. C. (1974). Retinal degeneration in monkeys induced by deficiencies of vitamin E or A. *Invest. Oothalmol, Vis, Sci,* 13,499–510.

Hertog M. G. L., Hollman P. C. H., Katan M. B., Kromhout D. (1993). Intake of potentially anticarcinogenic flavonoids and their determinants in adults in the Netherlands. *Nutr Cancer* 20, 1, 21–29.

Ichikawa, M. and Fijita, Y. (1987). Effects of nitrogen and energy metabolism on body weight in later life of male Wsitar rats consuming a constant amount of food. *J Nutr,* 117,1751–1758.

Jäger W., Buchbauer G., Jirovetz L., Dietrich H., Plank Ch (1992). Evidence of the sedative effect of neroli oil, citronellal and phenylethyl acetate on mice. *J Essent. Oil Res.* 4,387–394.

Malone M. J., Szoke M C. (1982). Neurochemical studies in ageing brain. I. Structural changes in myeline lipids. *J Gerontol* 37, 262–267.

Millward, D. J. and Waterlow, J. C. (1978). Effect of nutrition on protein turnover in skeletal muscle (rat). *Fed. Proc.,* 37, 2283–2290.

Munro, H. N. (1981). Nutrition and ageing. *Brit. Med. Bull.,* 37, 83–88.

Munro, H. N., and Young, V. R. (1978). Urinary excretion of N-methylhistidine (3-methylhistidine): a tool to study metabolic response in relation to nutrient and hormonal status in health and disease of man. *Am. J. Clin. Nutr.* 31, 1608–1614.

Newsome, D. A., Swartz, M., Leone, N. C., Eldton, R. C. and Miller E. (1988). Oral zinc in macular degeneration. *Arch Opthalmol,* 106, 192–198.

Neuringer, M., Anderson, G. J. and Connor, W. E. (1988). The essentially of n-3 fatty acids for the development and function of the retina and brain. *Ann, Rev, Nutr,* 8, 517–541.

Organisciak, D. T., Wang, H. M., Li, Z, Li, Z Y and Tso M. (1988). The protective effect of ascorbate in retinal light damage of rats. *Invest, Opthalmol Vis, Sci* 26, 1580–1588.

Penzes, L., Izsak J., and Beregi, E. changes of organ induces of CBA/Ca inbred mice as function of age. *Zeitsch. Gerontol.,* 22:170–174, 1989.

Penzes L., Noble R. C., Beregi E., Imre S., Izsák J., Régius O. (1988). Effect of 2-mercaptoethanol on some metabolic indices of ageing of CBA/Ca inbred mice. *Mech Age Develop* 45, 75–92.

Piretti, M. V. Paqliuca, G. and Vasina, M. (1988). Transmethylation of neutral and polar lipids with NaBH in the presence of NaOH. *Chem. Phys, Lipids,* 47, 149–153.

Prothro, J. (1989). Protein and amino acid requirements of the elderly. *Ann. NY Acad. Sci.,* 561, 143–156.

Santidrian, S., Burini, R. Munro, H. N. and Young, V. R. (1981). Urinary output of N-methylhistidine and hydroxyproline in mature and old male rats fed an adequate diet. *Rev. Esp. Fisiol.,* 37, 103–104.

Spackman, D. H., STein, W. H., More, S. (1958). Automatic recording apparatus for use in chromatography of amino acids. *Anal. Chem.,* 30, 1190–1206.

Sternberger L. A., Hardy P. H., Calculus J. L., Meyer H. G. (1970). The unlabelled antibody enzyme method of immunohistochemistry. Preparation and properties of soluble antigen antibody complex (horseradish peroxidase-antihorseradish peroxidase) and its use in identification of spirochetes. *J. Histochem Cytochem* 18, 315–333.

Strickland, K. P. The chemistry of phospholipids. In: Form and Function of Phospholipids, edited by Ansell, G. B., Dawson, R. M. C., and Hawthorne, J., Elsevier, Amsterdam, 1973, pp. 9–42

Summerfield, F. W., and Toppel, A. L. Effects of dietary polyunsaturated fats and vitamin E on ageing and peroxidative damage to DNA. *Arch. Biochem. Bio phys.,* 233:408–416, 1984.

Tischler, M. E. (1981). Hormonal regulation of protein degradation in skeletal and cardiac muscle. *Life Sci.,* 28, 2569–2576.

Tomas, F. M., Munro, H. N. and Young, V. R. (1979). Effect of glucocorticoid administration on the rate of muscle protein breakdown in vivo rats, as measured by urinary excretion of N-methylhistidine. *Biochem. J.* 178, 139–146.

Toda Sh, Miyase T., Arichi H., Tanizawa H., Takino Y. (1985). Natural antioxidants III. Antioxidative components isolated from rhizome of Curcuma Longa L. *Chem Parm Bull,* 33 1725–1728

Tso, M. O. (1985). Pathogenic factors of ageing macular degeneration. *Arch. Opthalmol* 92, 628–635

Vinding, T., Appleyard, M., Nyobe, J. and Jensen, G. (1992). Risk factor analysis for atrophic and exudative age-related macular degeneration. *Acta Opthalmol,* 70, 66–72.

Wada, E., and Tsumita, T. Ageing and compositional changes of rat lens. *Mech. Ageing Dev.,* 27:287–294, 1984.

Wilbur, K. M., Bernheim, F., and Shapiro, O. W. The thiobarbituric acid reagent as a test for the oxidation of unsaturated fatty acids by various agents. *Arch. Biochem. Biophys.,* 24:305–313, 1949.

Wilson, J. H. P., Swart, G. R. van den Berg, J. W. O. and Lamberts, S. W. J. (1981), the effects of triodothyronine on weight loss, nitrogen balance and muscle protein catabolism in obese patients on a very low calorie diet. *Nutr. Rep. Internat.,* 24, 145–151.

Wu T. W., Zeng L. H., WuJ, Fung K. P. (1993). Morin hydrate is a plant-derived and antioxidant based hepatoprotector. *Life Sci* 53, 13, 213–218.

Young, V. R. and Munro, H. N. (1978). N-Methylhistidine (3methylhistidine) and muscle protein turnover: An overview. *Fed. Proc.,* 37, 2291–2300.

TABLE 1.1

The fatty acid compositions (major acids weight percentage of total) of the phospholipid fraction of the livers from the young (6 months old) and ageing (22 months old) CBA/Ca mice.

| | Young Mice | | Ageing Mice | | | | | |
|---|---|---|---|---|---|---|---|---|
| | | | | Treated | | | | |
| Fatty Acid | Untreated | Treated | Untreated | Clove | Thyme | Nutmeg | Pepper | Almond |
| Palmitic | 26.2 ± 0.54 | 25.3 ± 0.89 | 38.3 ± 0.34[3] | 35.3 ± 1.00[a] | 31.6 ± 2.49[a] | 31.5 ± 1.28[c] | 29.2 ± 2.44[b] | 35.1 ± 2.55 |
| Palmitoleic | 1.98 ± 0.14 | 1.87 ± 0.05 | 2.70 ± 0.16[2] | 2.02 ± 0.10[b] | 1.54 ± 0.33[a] | 2.19 ± 0.13[a] | 1.85 ± 0.11[b] | 2.54 ± 0.13 |
| Stearic | 15.7 ± 0.69 | 14.6 ± 0.33 | 16.4 ± 0.44 | 14.8 ± 0.53 | 16.2 ± 1.74 | 13.5 ± 1.04[a] | 14.2 ± 0.51[a] | 16.0 ± 0.87 |
| Oleic | 14.9 ± 0.77 | 13.6 ± 0.47 | 17.9 ± 1.48 | 16.0 ± 1.34 | 13.3 ± 1.13[a] | 16.2 ± 1.03 | 15.5 ± 0.81 | 15.6 ± 0.49 |
| Linoleic | 18.6 ± 1.00 | 16.9 ± 0.25 | 14.1 ± 0.52[2] | 15.8 ± 0.61 | 16.5 ± 0.78[a] | 15.5 ± 1.07 | 18.2 ± 0.18 | 16.7 ± 0.82[a] |
| Linolenic | 0.60 ± 0.15 | 0.42 ± 0.03 | 0.70 ± 0.04 | 0.64 ± 0.09 | 0.35 ± 0.06[b] | 0.33 ± 0.06[c] | 0.42 ± 0.03[c] | 0.39 ± 0.09[a] |
| Eicosatrienoic | 2.04 ± 0.25 | 2.32 ± 0.11 | 0.76 ± 0.10[3] | 1.42 ± 0.36 | 1.08 ± 0.19 | 1.13 ± 0.12[a] | 1.62 ± 0.25[c] | 1.30 ± 0.17[a] |
| Arachidonic | 15.5 ± 0.91 | 16.5 ± 0.98 | 6.60 ± 0.44[3] | 10.3 ± 0.98[b] | 14.5 ± 1.89[b] | 14.0 ± 0.74[c] | 14.0 ± 1.09[c] | 9.12 ± 7.46 |
| Docosapentaenoic | 0.18 ± 0.07 | 0.28 ± 0.03 | <0.10 | 0.31 ± 0.08 | <0.10 | 0.17 ± 0.05 | 0.19 ± 0.07 | 0.10 |
| Docosahexaenoic | 3.86 ± 0.35 | 5.87 ± 0.64 | 1.68 ± 0.32[3] | 3.31 ± 0.32[b] | 4.33 ± 1.00[a] | 5.61 ± 0.64[c] | 5.34 ± 0.58[c] | 3.31 ± 0.70 |

Each result is the mean ± standard error of 10 observations.
Significance of difference, using Student's test, from young control mice: [1] = $P < 0.05$; [2] = $P < 0.01$; [3] = $P < 0.001$
Significance of difference from aged Control mice: [a] = $P < 0.05$; [b] = $P < 0.01$; [c] = $P < 0.001$

TABLE 1.2

Antioxidative properties of the volatile oil of *Thymus vulgaris* (thyme) and its main constituents.

| Oil Constituent | Zone of Colour Retention | Intensity |
|---|---|---|
| Whole oil | 25.0 | +++ |
| Borneol | 11.4 | + |
| Camphene | 16.2 | ++ |
| Carvacrol | 13.2 | +++ |
| β-Caryophyllene | 12.3 | ++ |
| 1,8-Cineole | Neg | Neg |
| p-Cymene | Neg | Neg |
| Linalool | 20.6 | ++ |
| Myrcene | 10.8 | ++ |
| Oct-1-en-3-ol | Neg | Neg |
| α-Pinene | Neg | Neg |
| β-Pinene | Neg | Neg |
| α-Terpinene | Neg | Neg |
| δ-Terpinene | 12.3 | ++ |
| Terpinen-4-ol | Neg | Neg |
| α-Thujone | Neg | Neg |
| β-Thujone | 19.3 | ++ |
| Thymol | 13.2 | +++ |

Diameter of zone of colour retention measured in mm:
colour intensity evaluated by + moderate, ++ average, +++ high, Neg Negative result.

TABLE 3.1

Percentage composition of the unsaturated fatty acid methyl esters in the retinas from rats fed the essential oils. Each result is for the pooled samples of the retinas from 6 rats per group.

| Treatment | Control | Almond | Clove | Nutmeg | Pepper | Thyme |
|---|---|---|---|---|---|---|
| palmitoleic | 6.55 | 3.09 | 1.96 | 1.72 | 1.94 | 3.28 |
| oleic | 30.14 | 35.02 | 22.18 | 22.76 | 23.38 | 25.00 |
| cis-vaccenic | 3.69 | 3.59 | 3.98 | 4.38 | 4.69 | 5.01 |
| linoleic | 7.02 | 3.79 | 2.32 | 2.64 | 3.08 | 2.78 |
| arachidonic | 12.41 | 13.49 | 15.98 | 15.98 | 18.50 | 17.51 |
| eicosamonoenoic | 1.00 | 0.99 | 0.37 | 0.89 | <0.10 | <0.10 |
| eicosapentaenoic | <0.10 | <0.10 | 0.57 | <0.10 | 0.67 | 0.67 |
| docosahexaenoic | 39.18 | 40.03 | 52.63 | 51.63 | 47.73 | 45.75 |

TABLE 1.3

Plant essential oils exhibiting antioxidative and pro-oxidative properties.

| | | | | | | | | | |
|---|---|---|---|---|---|---|---|---|---|
| Almond Bitter | + | Bay | + | Caraway | 0 | Clove | + | Fennel Sweet | 0 |
| Almond Sweet | 0 | Bergamot | − | Cardamon | − | Coriander | − | Geranium | 0 |
| Angelica | 0 | Calmus | + | Celery | + | Dill | 0 | Ginger | 0 |
| Anise | 0 | Chamomile | 0 | Cinnamon | + | Estragon | − | Laurel | + |
| Basil | 0 | Cananga | 0 | Citronella | + | Eucalyptus | − | Lavender | 0 |
| Lemon | 0 | Melissa | 0 | Parsley | + | Rosemary | + | Star Anise | 0 |
| Lime | − | Mint | + | Pepper | + | Sage | − | Thuja | − |
| Lovage | + | Nutmeg | + | Peppermint | + | St. J Wort | 0 | Thyme | + |
| Mandarin | 0 | Orange | 0 | Pimento | + | Sassafras | + | Valerian | − |
| Marjoram | 0 | Orange Bitter | 0 | Rose | + | Spike | + | Verbena | − |

+ Antioxidant activity;
− Pro-oxidative activity;
0 No activity

TABLE 4.1

Body and organ weights of rats at 28 months.

|  | Body weight | Brain | Lung | Heart | Spleen | Liver | Kidney (left) | Kidney (right) |
|---|---|---|---|---|---|---|---|---|
| Control | 239 ± 39.6 | 1.38 ± 0.03 | 4.37 ± 1.01 | 1.28 ± 0.05 | 0.42 ± 0.08 | 9.77 ± 1.52 | 1.15 ± 0.08 | 1.17 ± 0.07 |
| Almond | 293 ± 25.5 | 1.38 ± 0.03 | 4.39 ± 0.72 | 1.15 ± 0.07 | 0.32 ± 0.04 | 8.03 ± 1.13 | 1.09 ± 0.10 | 1.08 ± 0.11 |
| Clove | 311 ± 20.2 | 1.39 ± 0.02 | 4.20 ± 0.74 | 1.20 ± 0.11 | 0.46 ± 0.03 | 10.46 ± 1.30 | 1.21 ± 0.02 | 1.26 ± 0.12 |
| Nutmeg | 340 ± 30.7 | 1.43 ± 0.04 | 5.32 ± 1.15 | 1.33 ± 0.18 | 0.34 ± 0.04 | 10.17 ± 1.04 | 1.29 ± 0.07 | 1.31 ± 0.05 |
| Pepper | 290 ± 32.9 | 1.36 ± 0.06 | 4.32 ± 0.56 | 1.05* ± 0.06 | 0.29 ± 0.07 | 9.19 ± 1.54 | 1.22 ± 0.10 | 1.20 ± 0.12 |
| Thyme | 298 ± 40.5 | 1.33 ± 0.05 | 4.27 ± 0.54 | 1.01 ± 0.14 | 0.30 ± 0.04 | 7.08 ± 0.50 | 1.15 ± 0.09 | 1.15 ± 0.08 |

Each result is the mean ± standard error.
Significantly different from control * = $P < 0.05$.

TABLE 4.2

Absolute and relative urinary excretion ratios of 3-methyl-histidine.

|  | 3 methyl-histidine excretion | | Creatine excretion | Ratio 3-methyl-histidine/creatine |
|---|---|---|---|---|
|  | μmol per 24 h | μmol per kg body weight | mg per 24 h |  |
| Control | 3.08 ± 0.61 | 13.1 ± 2.86 | 7.72 ± 2.47 | 0.43 ± 0.07 |
| Almond | 2.86 ± | 8.14 ± | 9.83 ± | 0.29 ± |
| Clove | 2.50 ± 0.40 | 7.93 ± 0.87 | 10.9 ± 2.70 | 0.23 ± 0.03* |
| Nutmeg | 3.62 ± 0.42 | 11.8 ± 1.09 | 14.9 ± 0.75* | 0.24 ± 0.03 |
| Pepper | 3.34 ± 0.17 | 15.0 ± 2.86 | 9.86 ± 0.47 | 0.34 ± 0.01 |
| Thyme | 2.64 ± 0.16 | 9.33 ± 0.98 | 18.5 ± 1.72* | 0.15* ± 0.01 |

Each result is the mean ± standard error.
*Significantly different from control $P < 0.05$;
** significantly different from control $P < 0.01$.

We claim:

1. A method of producing elevated PUFA levels in nervous tissue in a human or animal body, said method comprising administering a plant volatile oil or an active constituent thereof to said body in a physiologically effective amount.

2. A method as claimed in claim 1, wherein the plant volatile oil or constituent thereof comprises oil selected from the group consisting of clove, nutmeg, pepper, thyme, paprika, oregano, marjoram, basil and French tarragon or constituents of such oils, or any mixture thereof.

3. A method as claimed in claim 1, wherein the PUFAs are n-3 PUFAs.

4. A method as claimed in claim 1, wherein the PUFAs comprise docosahexaenoic acid.

5. A method as claimed in claim 1, wherein the plant volatile oil or constituent thereof is combined with a pharmaceutical carrier or excipient.

6. A method as claimed in claim 1, wherein the plant volatile oil or constituent thereof is administered as an emulsion with an aqueous constituent.

7. A method as claimed in claim 1, wherein the plant volatile oil or constituent thereof is encapsulated.

8. A method as claimed in claim 1, wherein the plant volatile oil or constituent thereof is administered enterally, parenterally or topically.

9. A method of treating nervous tissue in a human or animal body, said method comprising administering a plant volatile oil or an active constituent thereof to said body, in an amount sufficient to elevate the PUFA levels in the nervous tissue.

10. A method as claimed in claim 9, wherein the plant volatile oil or constituent thereof is administered to the human or animal body in a daily amount of not less than 15 mg per 50 kg of body weight.

11. A method as claimed in claim 9, wherein the plant volatile oil or constituent thereof comprises oil selected from the group consisting of clove, nutmeg, pepper, thyme, paprika, oregano, marjoram, basil and French tarragon or constituents of such oils, or any mixture thereof.

12. A method as claimed in claim 9, wherein the PUFAs are n-3 PUFAs.

13. A method as claimed in claim 9, wherein the PUFAs comprise docosaexaenoic acid.

14. A method as claimed in claim 9, wherein the plant volatile oil or constituent thereof is combined with a pharmaceutical carrier or excipient.

15. A method as claimed in claim 9, wherein the plant volatile oil or constituent thereof is administered as an emulsion with an aqueous constituent.

16. A method as claimed in claim 9, wherein the plant volatile oil or constituent thereof is encapsulated.

17. A method as claimed in claim 9, wherein the plant volatile oil or constituent thereof is administered enterally, parenterally or topically.

18. A method as claimed in claim 9, wherein the nervous tissue is retinal tissue.

19. A method as claimed in claim 1, wherein the nervous tissue is retinal tissue.

* * * * *